United States Patent

Suda et al.

(10) Patent No.: US 8,470,144 B2
(45) Date of Patent: Jun. 25, 2013

(54) ELECTRODE DEVICE FOR AN ELECTROCHEMICAL SENSOR CHIP

(75) Inventors: Atsushi Suda, Tokyo (JP); Tatsuo Kimura, Tokyo (JP); Ryota Kunikata, Tokyo (JP); Kosuke Ino, Sendai (JP); Tomokazu Matsue, Sendai (JP)

(73) Assignees: Japan Aviation Electronics Industry, Limited, Tokyo (JP); National University Corporation Tohoku University, Miyagi (JP)

(*) Notice: Subject to any disclaimer, the term of this patent is extended or adjusted under 35 U.S.C. 154(b) by 0 days.

(21) Appl. No.: 13/311,255

(22) Filed: Dec. 5, 2011

(65) Prior Publication Data

US 2012/0160678 A1   Jun. 28, 2012

(30) Foreign Application Priority Data

Dec. 28, 2010   (JP) ................................. 2010-292512

(51) Int. Cl.
    *G01N 27/416*   (2006.01)
(52) U.S. Cl.
    USPC ............................. 204/287; 204/267; 439/87
(58) Field of Classification Search
    USPC ................. 204/424, 267, 286.1, 287, 290.01, 204/294; 439/44–48, 78, 85, 87
    See application file for complete search history.

(56) References Cited

U.S. PATENT DOCUMENTS 5,738,530 A * 4/1998 Schreiber et al. ............... 439/66

FOREIGN PATENT DOCUMENTS

| JP | 2573443 B | 8/1993 |
| JP | 2003-532090 A | 10/2003 |
| JP | 2005-034129 A | 2/2005 |
| JP | 2006-322813 A | * 11/2006 |
| JP | 2007-278981 A | 10/2007 |
| WO | 0183674 A1 | 11/2001 |

OTHER PUBLICATIONS

Outline of Tohoku University Micro System Integration Center Symposium held Dec. 6-8, 2010 in Sendai, Japan, (5 pages) and English translation (8 pages).

Tohoku University Micro System Integration Center Symposium, Activities in collaboration connection sheet for an electrochemical sensor chip (Connection sheet for a biochip), Japan Aviation Electronics Industry, Limited, Product Development Center, Dec. 6, 2010 (15 pages).

* cited by examiner

*Primary Examiner* — J. Christopher Ball
(74) *Attorney, Agent, or Firm* — Hovey Williams LLP

(57) ABSTRACT

An electrode device for an electrochemical sensor chip includes an insulation sheet having an insulating property and including a top surface and a bottom surface opposite to each other in a thickness direction, and electrode members having a conductivity and held by the insulation sheet in portions piercing the insulation sheet in a thickness direction, one ends of the electrode members located on the top surface side of the insulation sheet being connected to the analyte, other ends located on the bottom surface side of the insulation sheet being connected to the electrodes of the transducer, recesses for trapping the analyte being formed in the top surface of the insulation sheet so as to correspond to the electrode members, the one ends of the electrode members being exposed at a bottom of the recesses.

8 Claims, 5 Drawing Sheets

ELECTRODE DEVICE FOR AN ELECTROCHEMICAL SENSOR CHIP

BACKGROUND OF THE INVENTION

The present invention relates to an electrode device for an electrochemical sensor chip and particularly to a disposable electrode device for connecting any of analytes such as chemicals and biologically derived substances exemplified by DNA, proteins, antibodies, cells, and, microorganisms to the electrodes of a transducer for detecting an analyte with an enhanced sensitivity using an electrochemical method.

There are widely known in the fields of medicine, food, and environment techniques for detecting a trace amount of analyte existing in a sample with a high sensitivity. Generally, an electrochemical sensor chip comprises electrodes modified by a molecular recognition element formed of biologically derived substances, chemicals, and the like selectively reacting with an analyte in a sample. When a sample is brought into contact with these electrodes, effects produced by an interaction can be sensed by detecting a change in electric current using an electrochemical method with a high sensitivity if the sample contains a substance interacting with the molecular recognition element.

In the field of gene analyses that have made a rapid progress in recent years, trials are being made to determine DNA sequences by electrochemical methods using, for example, a technique described in JP 2573443 B. These methods enable high-sensitive analysis as to whether DNA, examined as an analyte, has a sequence that is capable of complementarily binding with probe DNA by converting one single stranded DNA obtained by denaturing the analyte DNA and another single stranded DNA having a known base sequence (probe DNA) into double-stranded DNA through hybridization, and then mixing therein an intercalated material specifically binding with double-stranded DNA and reversible with respect to redox reaction.

Electrochemical sensor chips widely use a flat electrode-type electrode device as described, for example, in JP 2007-278981 A to achieve contact with a sample. As illustrated in FIG. 15, this electrode device comprises a planar electrode 2 made of a conductive material formed on an insulation substrate 1. A sample is placed on the planar electrode 2, and the potential of the planar electrode 2 is extracted through a conductive pattern 3. The planar electrode 2 and the conductive pattern 3 can be formed by a printing method, for example, which reduces manufacturing costs so that the electrode device may be suitably used as a disposable electrode device for an electrochemical sensor chip.

JP 2003-532090 A describes another known example of electrochemical measurement, which uses an electrode formed on the surface of an integrated, circuit chip. As illustrated in FIG. 16, an electrode 5 is formed on the surface of an integrated circuit chip 4, and a sample 6 is placed on the electrode 5. In this case, an additional circuit for amplifying feeble current may be integrated into the integrated circuit chip 4, so that a highly-sensitive measurement can be expected.

SUMMARY OF THE INVENTION

However, in the electrode device as described in JP 2007-278981 A, the potential of the planar electrode device 2 in contact with a sample is extracted through the conductive pattern 3. Therefore, the electrode device necessarily has a long conduction path and is susceptible to electromagnetic noise and the like, possibly reducing the detection sensitivity.

In addition, since the planar electrode device 2 and the conductive pattern 3 are formed in a planar extension on the insulation substrate 1, the size of the electrode device is increased and, when performing multi-point measuring, the whole measuring device requires a large size.

On the other hand, when the sample 6 is a liquid sample containing a biologically derived, substance, etc., the integrated circuit chip 4 as described in JP 2003-532090 A may allow the sample 6 to infiltrate into the integrated circuit chip 4 through fine cracks or the like in the insulation layer film covering the surface of the integrated circuit chip 4, possibly causing short-circuiting and thus reducing the reliability of measurement. Further, the electrode 5 is secured to the surface of the integrated circuit chip 4 which is expensive, making it difficult for the electrode device to be used as a disposable product. Further, it is also impossible to dispose the electrode device by removing only the electrode 5 from the integrated circuit chip 4.

Thus, an object of the present invention is to provide an electrode device for an electrochemical sensor chip capable of highly-sensitive and highly-reliable measurement even when measuring a liquid sample and suitable for multi-point measurement and the use as a disposable product.

An electrode device for an electrochemical sensor chip according to the present invention comprises; an insulation sheet having an insulating property and including a top surface and a bottom surface opposite to each other in a thickness direction; and electrode members having a conductivity and held by the insulation sheet in portions piercing the insulation sheet in a thickness direction, one ends of the electrode members located on the top surface side of the insulation sheet being connected to an analyte, other ends located on the bottom surface side of the insulation sheet being connected to an electrodes of a transducer, recesses for trapping the analyte being formed in the top surface of the insulation sheet so as to correspond to the electrode members, the one ends of the electrode members being exposed at a bottom of the recesses.

DETAILED DESCRIPTION OF THE INVENTION

Embodiments of the present invention will be described below based on the appended drawings.

Embodiment 1

Figure 1:
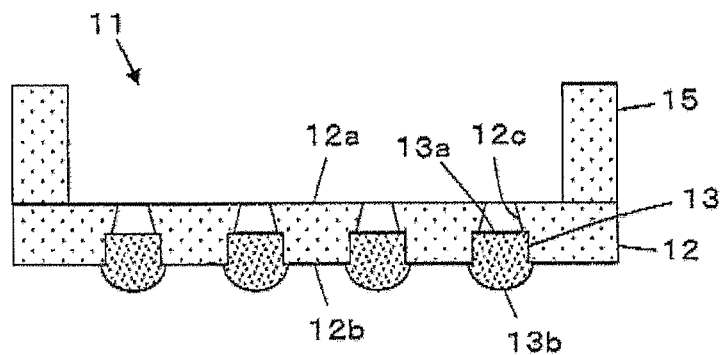
FIG. 1 is a cross section of an electrode device for an electrochemical sensor chip according to an embodiment 1 of the invention.

FIG. 1 illustrates a configuration of an electrode device 11 for an electrochemical sensor chip according to an embodiment 1 of the invention. The electrode device 11 for an electrochemical sensor chip comprises an insulation sheet 12 and electrode members 13 distributed in a matrix pattern at a given pitch in the insulation sheet 12. The insulation sheet 12 is made of an insulating material and comprises a top surface 12a and a bottom surface 12b opposite to each other in a thickness direction. The electrode members 13 are made of a conductive material and held by the insulation sheet 12 so as to pierce the insulation sheet 12 in the thickness direction. There are formed in the top surface 12a of the insulation sheet 12 a plurality of recesses 12c so as to correspond to the electrode members 13, and one ends 13a of the electrode members 13 are exposed at the bottom of the respective recesses 12c. The recesses 12c of the insulation sheet 12 are provided to trap an analyte and have a reversely tapered shape such that the diameter thereof at the bottom is larger than the diameter of an opening thereof that opens at the top surface 12a of the insulation sheet 12. The other ends 13b of the electrode members 13 project outwardly from a bottom surface 12b of the insulation sheet 12.

Figure 2:
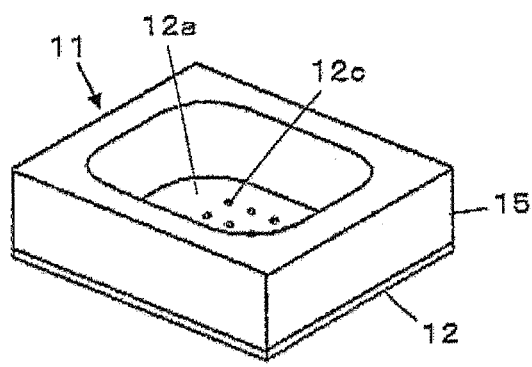
FIG. 2 is a perspective view of the electrode device for an electrochemical sensor chip according to the embodiment 1 of the invention.

An annular liquid reservoir member 15 is provided on the periphery of the top surface 12a of the insulation sheet 12. The liquid reservoir member 15 surrounds all the recesses 12c corresponding to the electrode members 1a on the top surface side of the insulation sheet 12 as illustrated in FIG. 2.

Figure 3:
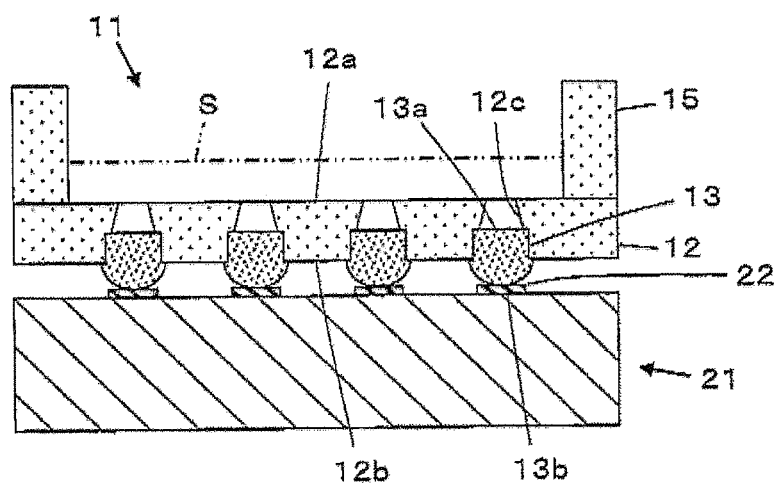
FIG. 3 is a cross section of an electrochemical sensor chip using the electrode device for an electrochemical sensor chip according to the embodiment 1.

The electrode device 11 for an electrochemical sensor chip having the above configuration is disposed immediately on a transducer 21 for use as illustrated in FIG. 3.

The transducer 21 is formed of an LSI chip and comprises electrodes 22 distributed in a matrix pattern on the top surface thereof. The electrodes 22 are disposed at a given pitch that is the same as the given pitch of the electrode members 13 provided on the electrode device 11 for an electrochemical sensor chip, so that the electrode members 13 provided on the electrode device 11 are in one-to-one correspondence with the electrodes 22 of the transducer 21.

The other ends 13b of the electrode members 13 of the electrode device 11 for an electrochemical sensor chip come into contact with the respective electrodes 22 of the transducer 21 to establish electrical connection. Then, a liquid sample S containing an analyte is reserved in the liquid reservoir member 15 of the electrode device 11 for an electrochemical sensor chip. The one ends 13a of the electrode members 13 exposed at the bottom of the respective recesses 12c of the insulation sheet 12 are previously modified by a molecular recognition element formed of biologically derived substances or the like that selectively react with an analyte existing in the liquid sample S, so that a change in electric current or the like that is electrochemically caused as the analyte such as cells in the liquid sample S reacts with the molecular recognition element is transmitted to the electrodes 22 of the transducer 21 through the electrode members 13, whereupon the transducer 21 detects the analyte in the liquid sample S with a high sensitivity.

Now, with the one ends 13a of the electrode members 13 exposed at the bottom of the respective recesses 12c of the insulation sheet 12, the analyte such as cells existing in the liquid sample S can be readily trapped in the recesses 12c and held on the one ends 13a of the electrode members 13, leading to an enhanced reliability in the analyte detection.

Instead of the one ends 13a of the electrode members 13 being modified by a molecular recognition element, beads previously modified by a molecular recognition element may be held the surface of the one ends 13a of the electrode members 13 to likewise achieve detection of the analyte. Also in this case, with the recesses 12c formed in the insulation sheet 12 for the respective electrode members 13, beads previously modified by a molecular recognition element can be readily held on the surface of the one ends 13a of the electrode members 13, enabling analyte detection with an enhanced reliability.

According to the embodiment 1, the reversely tapered shape in articular of the recesses 12c having a larger diameter at the bottom than at the opening that opens at the top surface 12a of the insulation sheet 12 effectively precludes the analyte such as cells, beads modified by a molecular recognition element, and the like once trapped in the recesses 12c from escaping from the recesses 12c, thereby increasing the measuring reliability.

The material of the insulation sheet 12 of the electrode device 11 for an electrochemical sensor chip may be a silicone rubber. Other examples, thereof include resin materials such as acrylic and polycarbonate, glass, and ceramics.

The electrode members 13 are made of a conductive material and may, for example, be made of a silicone based material containing conductive filler such as Ag. Alternatively, the electrode members 13 may be formed of a metallic material having an excellent conductivity such as a metallic material having an Au coated surface.

However, at least one of the insulation sheet 12 and the electrode members 13 preferably have elasticity in order to establish a good electric connection between the electrode members 13 held by the insulation sheet 12 and the electrodes 22 of the transducer 21. Such a configuration absorbs variation in height of the other ends 13b of the electrode members 13 and variation in height of the surfaces of the electrodes 22 of the transducer 21 arising in manufacture and establishes a good electric connection between them, enabling measuring with higher accuracy and enhanced reliability.

When the electrode member 13 has elasticity, the whole of the electrode member 13 need not necessarily have elasticity and it suffices when at least the other ends 13b of the electrode members 13 in contact with the electrodes 22 of the transducer 21 have elasticity.

When the insulation sheet 12 has elasticity, if the bottom surface 12b of the insulation sheet 12 has an adhesion, applying a load from above onto the electrode device 11 for an electrochemical sensor chip placed on the transducer 21 allows the bottom surface 12b of the insulation sheet 12 to adhere to the surface of the transducer 21 and be secured, thus establishing the electrical connection between the electrode members 13 and the electrodes 22 of the transducer 21 with yet further enhanced reliability.

Preferably, the electrode members 3 are held, in intimate contact with the insulation sheet 12 in order to prevent the liquid sample S contained in the liquid reservoir member 15 from leaking to the bottom surface side of the insulation sheet 12 through the interfaces between the insulation sheet 12 and the electrode members 13. Accordingly, using the same material ingredients to form the insulation sheet 12 and the electrode members 13 is effective. For example, the insulation sheet 12 made of silicone rubber may hold the electrode members 13 made of a material whose main ingredient is a silicone-based substance.

The intimate contact required between the electrode members 13 and the insulation sheet 12 is sufficient if the liquid sample S does not leak or penetrate through the interfaces between them and gas may flow therethrough even in the presence of small gaps between the electrode members 13 and the insulation sheet 12, such intimate contact between them sufficient to preclude the liquid sample S from leaking or penetrating can be achieved by forming coating films on these interfaces that have a low affinity with the liquid sample S or by forming an asperity on the interfaces to reduce the wettability in relation to the liquid sample S.

Depending on the material used to form the electrode members 13, the one ends 13a of the electrode members 13 exposed at the bottom of the recesses 12c of the insulation sheet 12 are preferably covered by, for example, a biocompatible coating formed by applying a carbon paste in order to achieve a chemically stable contact between the one ends 13a of the electrode members 13 and the analyte in the liquid sample S. While the biocompatible coating may be otherwise formed by using chemically stable metals such as Au and Pt, a carbon paste, which is inexpensive, is a preferred material when the electrode device 11 for an electrochemical sensor chip is used as a disposable device.

As described above, the electrode device 1 electrochemical sensor chip according to the embodiment 1 is disposed immediately on the transducer 21, and the electrode members 13 held by the insulation sheet 12 are brought into contact with the electrodes 22 of the transducer 21 to achieve reduction of the conduction path, which reduces the effects produced by, for example, electromagnetic noise, which in turn reduces adverse effects on measuring sensitivity, and hence achieves enhancement of measuring sensitivity. In addition, the configuration of the electrode members 13 being distributed in a matrix pattern so as to correspond to the positions of the electrodes 22 of the transducer 21 enables production of a measuring device having a compact planar size and capable of simultaneous multi-point measuring at the same time. Further, because the insulation sheet 12 and the electrode members 13 are in intimate contact, and the liquid sample S such as electrolyte solution used as specimen is not in immediate contact with the transducer 21, short-circuiting in the circuits inside the transducer 21 cannot occur and thus reliability is enhanced.

Further, because the one ends 13a of the electrode members 13 are exposed at the bottom of the respective recesses 12c of the insulation sheet 12, the analyte such as cells existing in the liquid sample S, beads previously modified by a molecular recognition element, etc. can be readily trapped in the recesses 12c and held on the top of the one ends 13a of the electrode members 13, ensuring further enhanced measuring reliability.

The electrode device 11 for an electrochemical sensor chip described above may be produced as follows.

Figure 4:
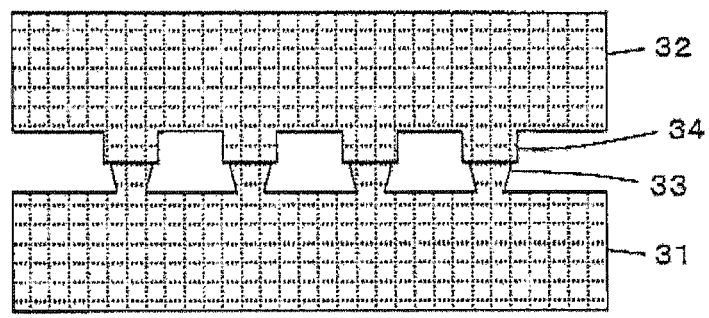
FIG. 4 is a cross section of a mold for producing an insulation sheet used in the embodiment 1.

First, a first mold 31 and a second mold 32 both made of Si and each having a protrusion structure for forming the insulation sheet 12 are produced as illustrated in FIG. 4. The protrusion structure of the first mold 31 is provided to form the recesses 12c and comprises protrusions 33 each having a tapered cylindrical shape with an upper diameter of 100 µm, a lower diameter of 90 µm, and a height of 100 µm and distributed in a matrix pattern having the same array pitch as the electrode 22 of the transducer 21. The protrusion structure of the second mold 32, on the other hand, is provided to form holes into which the electrode members 13 are filled and comprises protrusions 34 each having a cylindrical shape with a diameter of 140 µm and a height of 100 µm and distributed in the same pattern as the protrusions 33 of the first mold 31.

When only a part of the electrodes 22 of the transducer 21 are used for measuring, the first mold 31 and the second mold 32 to be produced may have the protrusion structure according to the positions of the electrodes 22 that are used for measuring.

The first mold 31 may be produced by machining a flat Si plate using deep etching through so-called Bosch process whereby a structure of the order of micrometers can be readily produced. The etching through Bosch process basically consists of two repeated processes of etching process and etching side wall protecting process. The etching process includes isotropic etching mainly using sulfur hexafluoride ($SF_6$) and, when there is a protection film on an etched bottom surface, the protection film is removed. On the other hand, in the etching side wall protecting process, a gas such as $C_4F_8$ or the like is used to protect the side walls to limit lateral etching. Balance between the two repeat processes enables control of the side wall inclination.

According to the embodiment 1, the time ratio of the etching process to the etching side wall protecting process is increased as compared with when upright side walls are to be formed to perform excessive etching of side walls to achieve formation of the protrusions 33 having a tapered cylindrical shape as illustrated, in FIG. 4.

Alternatively, a metal mold having such a protrusion structure may be produced by precision cutting or etching a metal plate.

The shape of the protrusions 34 of the second mold 32 is not limited to a cylindrical shape, provided that the shape permits filling of the electrode members 13. However, the cylindrical shape is preferred in order to facilitate filling of the electrode members 13. The second mold 32 may be produced likewise as the first mold 31 by machining a flat Si plate using deep etching through Bosch process. Alternatively, a metal mold may be produced by precision cutting or etching a metal plate.

Figure 5:
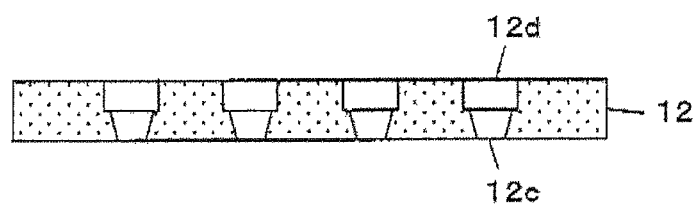
FIG. 5 is a cross section of the insulation sheet used in the embodiment 1.

To improve the demolding property of a molded product, a fluororesin-based demolding agent is applied to the surfaces of the first mold 31 and the second mold 32 on which the protrusion structure is each formed, and the two molds are positioned on and pressed to each other, whereupon a thermosetting, two-component, addition polymer-type silicone rubber yet to be hardened is injected between the molds 31 and 32. The procedure is followed by heating in an oven at 120° C. for 60 minutes to harden the silicone rubber, whereupon the molded product is released from the first mold 31 and the second mold 32. FIG. 5 illustrates the insulation sheet 12 formed in this manner. The recesses 12C corresponding to the protrusion structure of the first mold 31 and recesses 12d corresponding to the protrusion structure of the second mold 32 are formed in a matrix pattern respectively on the top surface side and the bottom surface side to create throughholes formed by the recesses 12c and the recesses 12d connected with each other.

Figure 6:
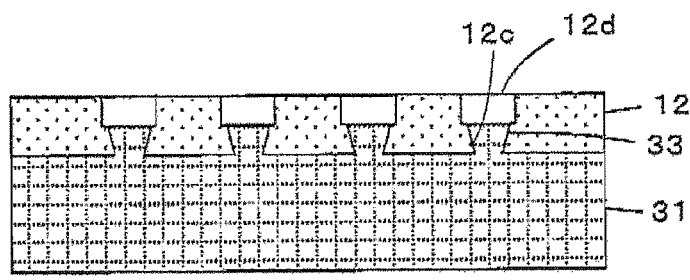
FIG. 6 is a cross section of the insulation sheet used in the embodiment 1 as fitted with a mold.

Next, as illustrated in FIG. 6, the insulation sheet 12 is fitted again with the first mold 31 so that the recesses 12c of the insulation sheet 12 engage with the protrusions 33 of the first mold 31.

Figure 7A:
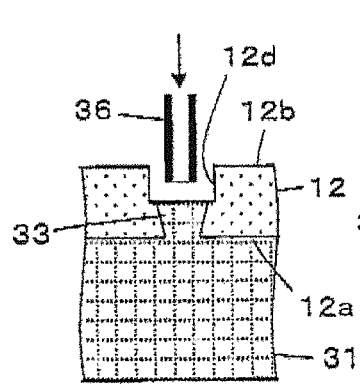
FIG. 7 is a cross section showing the steps of a method of producing electrode members.
Figure 7B:
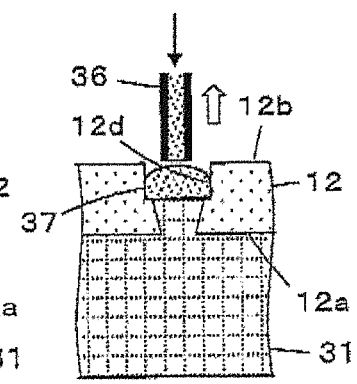
Figure 7C:
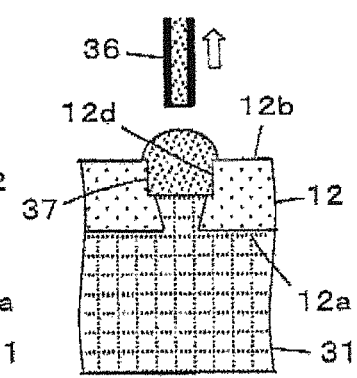

Then, as illustrated in FIG. 7A, an injection tube 36 of a dispenser is inserted into each of the recesses 12d from the bottom surface side of the insulation sheet 12, now turned to face upward, to inject a conductive material 37 composed of silicone-based material containing conductive filler such as Ag. The injection tube 36 of the dispenser has a tip whose outer diameter is smaller than the diameter 140 μm of the recesses 12d. The tip of the injection tube 36 is inserted to a depth of 50 μm from the bottom surface 12b of the insulation sheet 12, i.e., halfway through the depth of the recesses 12d, and thus injection is started. Then, as illustrated in FIG. 7B, injection of the conductive material 37 is continued as the injection tube 36 is gradually lifted. Thus, the conductive material 37 can be allowed to project upwardly from the bottom surface 12b of the insulation sheet 12 as illustrated in FIG. 7C.

Figure 8:
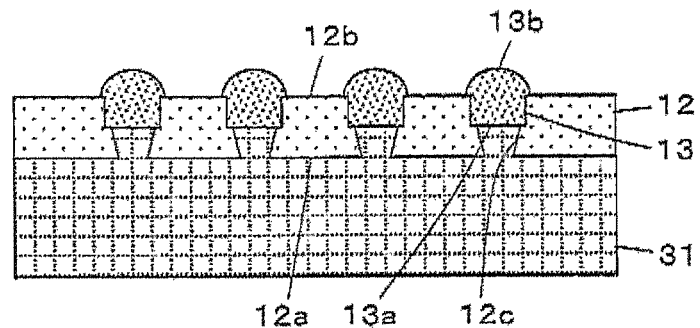
FIG. 8 is a cross section of the electrode members of which the formation has been completed.
Figure 9:
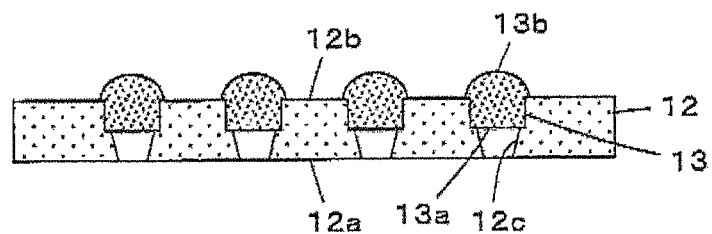
FIG. 9 is a cross section of the insulation sheet with electrode members used in the embodiment 1.

The procedure is followed by heating in an oven at 100° C. for 30 minutes to harden the conductive material 37. Thus, after producing electrode members 13 as illustrated in FIG. 8, the first mold 31 fitted to the insulation sheet 12 is withdrawn from the insulation sheet 12. Thus, the insulation sheet 12 holding therein the electrode members 13 is produced as illustrated in FIG. 9. The one ends 13a of the electrode members 13 are exposed at the bottom of the recesses 12c of the insulation sheet 12 while the other ends 13b project from the bottom surface 12b, of the insulation sheet 12.

Now, when a silicone based material containing conductive filler as conductive material for forming the electrode members 13 is selected, a good adhesion are ensured between the insulation sheet 12 made of silicone rubber and the electrode members 13.

Figure 10:
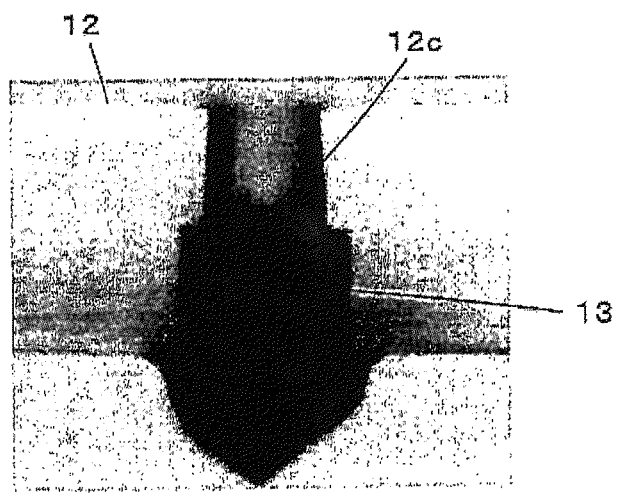
FIG. 10 is a photograph illustrating the insulation sheet in which electrode members, of which one is shown, have been formed.

FIG. 10 illustrates the insulation sheet 12 actually formed in this manner. As shown, a recess 12c with a reversed tapered shape having an upper diameter of 90 μm, a lower diameter of 100 μm, and a height of 100 μm is formed immediately on an electrode member 13.

Further, the annular liquid reservoir member 15 made of silicone rubber is adhered to the periphery of the top surface 12a of the insulation sheet 12 by silicone rubber yet to be hardened, followed by heating and hardening in an oven at 100° C. for 60 minutes. Thus, the electrode device 11 for an electrochemical sensor chip as illustrated in FIG. 1 is produced.

According to the embodiment 1, wherein the insulation sheet 12 is an elastic body made of silicone rubber, there is no fear of the reversely tapered recesses 12c being broken upon detaching the first mold 31 comprising the protrusions 33 having the shape of a tapered cylinder, but the recesses 12c having a greater tapering angle can be produced using a material having a greater flexibility.

Embodiment 2

Figure 11:
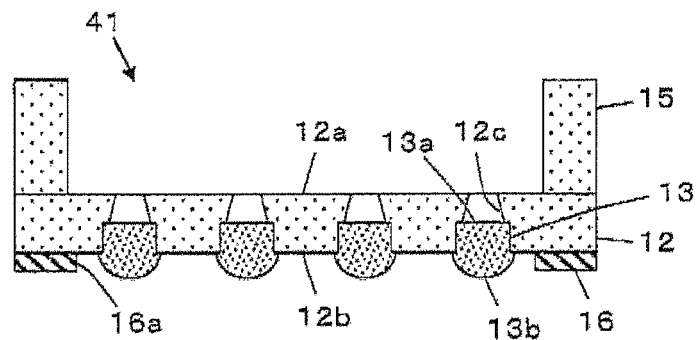
FIG. 11 is a cross section of an electrode device for an electrochemical sensor chip according to the embodiment 2.
Figure 12:
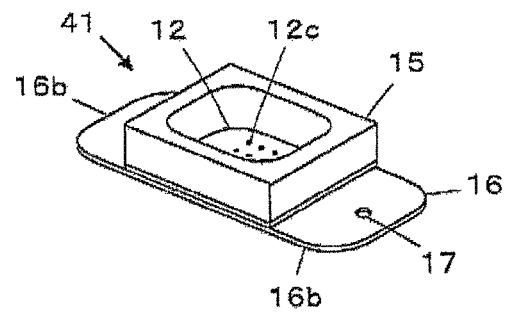
FIG. 12 is a perspective view of an electrode device for an electrochemical sensor chip according to the embodiment 2.

FIG. 11 illustrates a configuration of an electrode device 41 for an electrochemical sensor chip according embodiment 2. The electrode device 41 for an electrochemical sensor chip is equivalent to the electrode device 11 illustrated in FIG. 1 according to the embodiment 1 except that it additionally comprises a rigid frame 16 attached to the bottom surface 12b of the insulation sheet 12 in a position close to the periphery thereof. The frame 16 has the shape of a flat sheet having an opening 16a for exposing the other ends 13b of all the electro members 13 projecting from the bottom surface 12b of the insulation sheet 12 and comprises a pair of extensions 16b extending beyond the insulation sheet 12 and the liquid reservoir member 15 as illustrated in FIG. 12. The extensions 16b each have a positioning hole 17.

Figure 13:
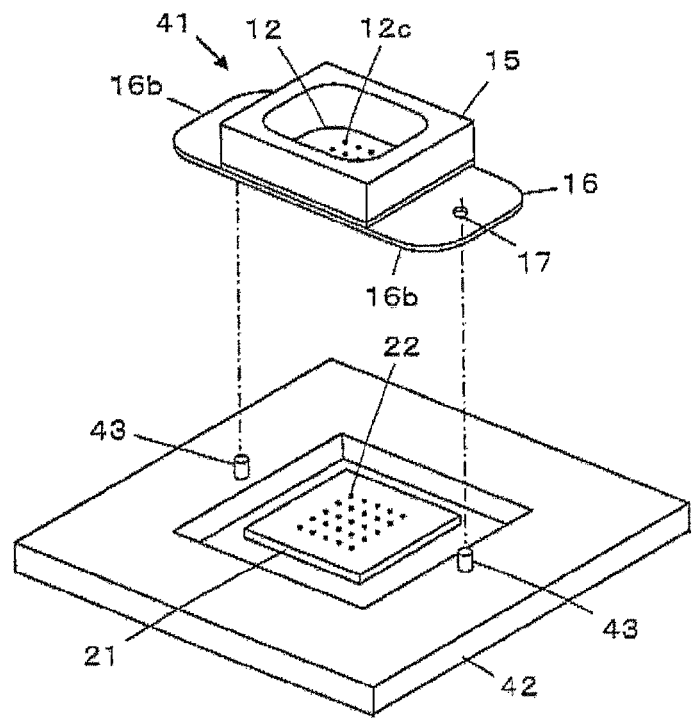
FIG. 13 is a perspective view of the electrode device for an electrochemical sensor chip according to the embodiment 2 as it is mounted to a transducer.

According to the embodiment 2, the transducer 21 is secured to a fixing base 42, and a pair of positioning pins 43 project from the fixing base 42 on the opposite sides of the transducer 21 as illustrated in FIG. 13.

Figure 14:
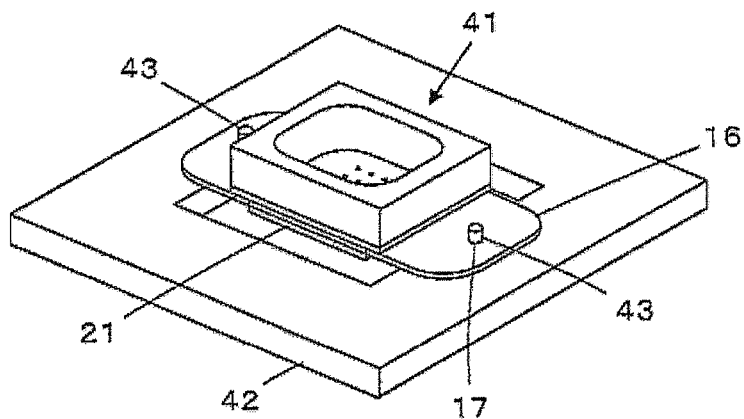
FIG. 14 is a perspective view of an electrochemical sensor chip using the electrode device for an electrochemical sensor chip according to the embodiment 2.
Figure 15:
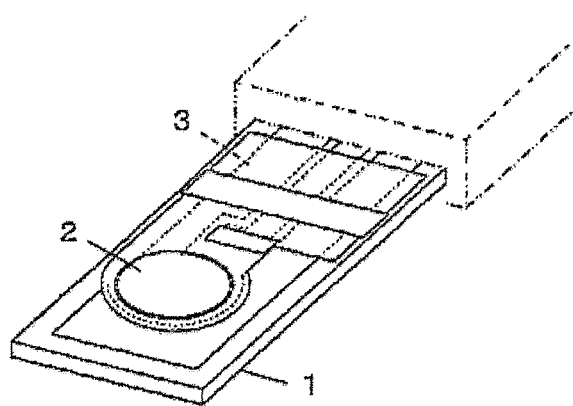
FIG. 15 is a perspective view of a conventional electrode device for an electrochemical sensor chip.
Figure 16:
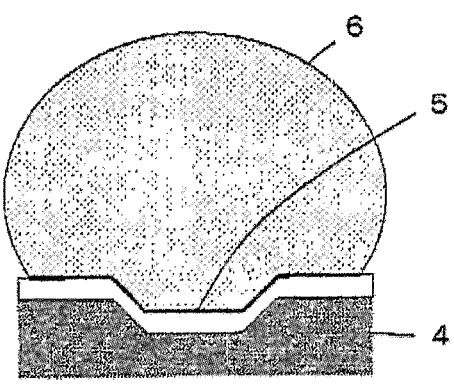
FIG. 16 is a cross section of a part of another conventional electrode device for an electrochemical sensor chip.

As illustrated, in FIG. 14, the electrode device 41 for an electrochemical sensor chip and the transducer 21 can be positioned with respect to each other by inserting a pair of the positioning pins 43 of the fixing base 42 through the positioning holes 17 of the frame 16 of the electrode device 41 for an electrochemical sensor chip.

Even when the disposable electrode device 41 for an electrochemical sensor chip is replaced with a new one, the electrode device 41 for an electrochemical sensor chip and the transducer 21 can be readily positioned with respect to each other by inserting the positioning pins 43 of the fixing base 42 through the positioning holes 17 of the frame 16, provided that the electrodes 22 of the transducer 21 have been previously positioned with accuracy in relation to the positioning pins 43 of the fixing base 42 when mounting the transducer 21 on the fixing base 42, and that electrode members 13 of the electrode device 41 for an electrochemical sensor chip have been previously positioned with accuracy in relation to the positioning holes 17 of the frame 16.

The frame 16 may be made, for example, of an 80-μm thick stainless steel plate and can be attached to the bottom surface 12b of the insulation sheet 12 by insert-molding the frame 16 when forming the insulation sheet 12 using the molds 31 and 32 as described in the embodiment 1.

The diameter of the positioning holes 17 of the frame 16 and the diameter of the positioning pins 43 of the fixing base 42 may be each 1 mm, for example.

Use of the frame 16 having such a rigidity not only enables positioning of the electrode members 13 of the electrode device 41 for an electrochemical sensor chip and the electrodes 22 of the transducer 21 but facilitates handling of the electrode device 41 for an electrochemical sensor chip even when the insulation sheet 12 is made of a material having an enhanced flexibility such as silicone rubber.

What is claimed is:

1. An electrode device for an electrochemical sensor chip for electrically connecting an analyte to electrodes formed on a surface of a transducer, comprising:
    an insulation sheet having an insulating property and including a top surface and a bottom surface opposite to each other in a thickness direction; and
    electrode members having a conductivity and held by the insulation sheet in portions piercing the insulation sheet in a thickness direction, one ends of the electrode members located on the top surface side of the insulation sheet being connected to the analyte, other ends located on the bottom surface side of the insulation sheet being connected to the electrodes of the transducer,
    recesses for trapping the analyte being formed in the top surface of the insulation sheet so as to correspond to the electrode members, the one ends of the electrode members being exposed at a bottom of the recesses,
    wherein the recesses have a reversely tapered shape having a larger diameter at a bottom than at an opening that opens at the top surface of the insulation sheet.

2. The electrode device for an electrochemical sensor chip according to claim 1, wherein the other ends of the electrode members each have a projecting portion protruding from the bottom surface of the insulation sheet.

3. The electrode device for an electrochemical sensor chip according to claim 2, wherein at least the projecting portion of each of the electrode members have elasticity.

4. The electrode device for an electrochemical sensor chip according to claim 1, wherein the insulation sheet has elasticity.

5. The electrode device for an electrochemical sensor chip according to claim 4, wherein the bottom surface of the insulation sheet has an adhesion.

6. The electrode device for an electrochemical sensor chip according to claim 1, wherein the electrode members are in intimate contact with the insulation sheet so that a liquid sample containing the analyte does not leak to the bottom surface side of the insulation sheet.

7. The electrode device for an electrochemical sensor chip according to claim 1, further comprising a liquid reservoir member provided on a periphery of the top surface of the insulation sheet.

8. The electrode device for an electrochemical sensor chip according to claim 1, further comprising a rigid frame attached to a periphery of the bottom surface of the insulation sheet.

* * * * *

UNITED STATES PATENT AND TRADEMARK OFFICE
CERTIFICATE OF CORRECTION

PATENT NO. : 8,470,144 B2  
APPLICATION NO. : 13/311255  
DATED : June 25, 2013  
INVENTOR(S) : Suda et al.

Page 1 of 1

It is certified that error appears in the above-identified patent and that said Letters Patent is hereby corrected as shown below:

In the Specification

Column 3, line 46, the phrase "electrode members 1a" should read: -- electrode members 13 --

Column 4, line 29, the phrase "articular" should read: -- particular --

Column 5, line 3, the phrase "electrode members 3" should read: -- electrode members 13 --

Column 5, line 17, the phrase "therethrough even in" should read: -- therethrough. Even in --

Column 5, line 37, the phrase "electrode device 1" should read: -- electrode device 11 --

Column 8, lines 2-3, the phrase "electro members 13" should read: -- electrode members 13 --

Signed and Sealed this
Twenty-second Day of October, 2013

Teresa Stanek Rea
*Deputy Director of the United States Patent and Trademark Office*